United States Patent [19]
Kellerman

[11] Patent Number: 5,154,682
[45] Date of Patent: Oct. 13, 1992

[54] LOW FRICTION ADJUSTABLE SHOE INSERT

[76] Inventor: David Kellerman, 1509 Shoreline Dr., Santa Barbara, Calif. 93109

[21] Appl. No.: 690,661

[22] Filed: Apr. 24, 1991

Related U.S. Application Data

[63] Continuation of Ser. No. 407,145, Sep. 14, 1989, abandoned.

[51] Int. Cl.⁵ .................. A43B 13/40; A43B 13/38
[52] U.S. Cl. ................................. 36/44; 36/71; 36/178
[58] Field of Search .................. 36/43, 44, 71, 10, 95, 36/130, 145, 155; 128/619

[56] References Cited

U.S. PATENT DOCUMENTS

| | | | |
|---|---|---|---|
| 88,494 | 3/1869 | Lowrey | 36/10 |
| 1,780,574 | 11/1930 | Williams | 36/44 |
| 2,776,500 | 1/1957 | Gonsalves | 36/10 |
| 2,853,805 | 9/1958 | Dratman | 36/10 |
| 2,928,193 | 3/1960 | Kristan | 36/44 |
| 3,071,877 | 1/1963 | Stickles | 36/44 |
| 3,143,812 | 8/1964 | Bittner | 128/596 |
| 3,195,244 | 7/1965 | Whitcas | 36/130 |
| 3,672,077 | 6/1972 | Coles | 36/130 |
| 4,694,590 | 9/1987 | Greenawalt | 36/44 |
| 4,793,078 | 12/1988 | Andrews | 36/44 |
| 4,813,157 | 3/1989 | Boisvert et al. | 36/44 |
| 4,928,404 | 5/1990 | Scheuermann | 36/95 |
| 4,930,232 | 6/1990 | Engle | 36/71 |

Primary Examiner—Steven N. Meyers
Attorney, Agent, or Firm—Marvin E. Jacobs

[57] ABSTRACT

A low friction shoe insert of ultrahigh molecular weight polyethylene or the like having a coefficient of friction of 0.3 or less with an array of detachable discrete cushion elements on the shoe contacting lower surface to both frictionally anchor the insert to the shoe and permit the shape to be customized to the wearers foot and selectively relieve pressure on painful and sensitive areas.

1 Claim, 6 Drawing Sheets

LOW FRICTION ADJUSTABLE SHOE INSERT

This is a continuation of application Ser. No. 07/407,145, filed Sept. 14, 1989.

TECHNICAL FIELD

This invention relates to a shoe insert for enhancing comfort and health. More particularly, this invention relates to an adjustable thickness insert with a very low friction foot contacting surface that alleviates symptoms of foot irritation and foot disease.

BACKGROUND OF THE INVENTION

Foot diseases ranging from minor irritation, rashes, callouses, corns, bunions, and ingrown toe nails to more severe traumatic conditions such as heel spurs are endemic. Many of these conditions are hereditary. However, all of these traumatic conditions are aggravated by rubbing and abrasion. Many of these conditions are solely attributable to irritation caused by abrasion. Often, people suffer from irritation even when wearing the best made shoes and using special shoe inserts such as arch supports.

Doctors of Medicine (M.D.) and of Podiatry Medicine (D.P.M.) are available for consultation and treatment of foot problems. A sub-specialty, Sport Medicine, has recently been recognized that also frequently deals with the feet. The most common problems are heel spurs, corns, callouses and bunions on the ball of the foot. The usual therapy is surgical removal, sometimes followed or preceded by prescriptions of a biomechanical device.

A very popular biomechanical device that is commonly prescribed is an orthotic. Orthotics are designed to correct the angular relationships between the various parts of the foot resulting in more normal functioning of the feet and legs. The objective of an orthotic is to decrease or eliminate foot symptoms, corns and callouses. But these devices are uncomfortable, fairly expensive, and require a long period of adjustment. Therefore, most patients buy only one pair and move them from shoe to shoe as needed. Although these devices provide a more anatomically correct alignment of the feet and a reduction in pressure on stress points, they do not eliminate frictional irritation of the feet.

It has been discovered that even with the best protonation and adjustment of the foot, the foot still moves slightly in the shoe, relative to the interior surface, leading progressively to discomfort, irritation, and finally trauma. Also, with time, the foot may change shape slightly, requiring a corresponding modification of the orthotic device which adds to the expense.

Shoe inserts have been provided in the past and it has been recognized that the use of smooth surfaced materials can increase comfort.

| List of Prior Art | |
| --- | --- |
| U.S. Pat. Nos. | Patentee |
| 246,454 | E. C. Bruen |
| 357,772 | G. H. Jones |
| 1,736,245 | M. M. Basar, Jr. |
| 1,838,487 | H. Josephs |
| 2,463,296 | A. A. Moore |
| 2,584,516 | D. S. Veatch |
| 2,795,865 | M. Backiel |
| 2,998,311 | W. M. Scholl |
| 2,853,805 | M. B. Dratman |
| 3,243,901 | G. Clarizio |
| 4,642,916 | V. B. Collins |

DESCRIPTION OF THE PRIOR ART

Scholl covers the outer face of the sole portion of a slipper with a sliok, smooth, non-skid covering such as a silky-finished fabric. Backiel uses a thin transparent, highly pliable plastic in his shoe insert. Clarizio prevents friction on the foot of the user by means of the gentle clinging action of a stretchable fabric. Collins uses a heel insert smoothly finished with PVC or other plastic to prevent stocking snags. Veatch's hosiery protector use a smooth plastic interior surface.

None of these references disclose the use of an adjustable thickness very low friction insert which unexpectedly results in causing traumatic foot conditions such as corns to recede and, in some cases, be totally eliminated.

SUMMARY OF THE INVENTION

The shoe insert of this invention has a foot contacting surface with an extremely low coefficient of friction. It has surprisingly been discovered that not only is comfort increased and irritation eliminated, but chronic conditions such as callouses and bunions are found to recede thus eliminating the need for surgery. Other conditions such as bone spurs become less irritated and painful allowing a wider range of activities.

For the purposes of this specification, and the claims appended hereto, the terms: low friction and low coefficient of friction, refer to the ratio of the force required to slide or start sliding one surface over another surface to a force pressing the two surfaces together. This is the standard definition found in all physics texts and reference books. The ratio, or coefficient has been found to be relatively constant, that is, independent of the absolute value of the force. A standard testing method has been established to measure these coefficients, namely, ASTM D 1894, which slides the material in question over a standard polished stainless steel surface. The coefficient of friction discussed herein is the coefficient as measured by ASTM D 1894. However, it should be understood that, in general, if a material has a low coefficient of friction on steel, it has a low coefficient of friction when sliding on any other material as well.

Friction arises primarily from microscopic surface irregularities that snag and grab irregularities on any surface sliding thereagainst. Thus, smoother surfaces have lower coefficients. But for a surface to remain smooth, it must be quite hard so that irregularities on a contacting surface do not sink into the smooth surface turning it into an irregular surface. Steel is hard and therefore makes a good test standard. But steel would, of course, make a poor and uncomfortable shoe insert because of its rigidity and hardness.

The shoe insert of this invention has a coefficient of friction of no more than 0.3. The materials found most useful to achieve this low coefficient are formed of fluorinated hydrocarbon polymers such as polytetrafluoroethylene (Teflon or TFE) and especially ultra high molecular weight (UHMW) polyethylene, suitably having a molecular weight above $2 \times 10^6$ usually about $4 \times 10^6$. This is about ten times higher than high density polyethylene (HDPE). UHMW polyethylene has the desirable and unique property of being dense enough to resist the sinking in of irregularities of a contacting surface and thus becoming less smooth and more frictional. Yet UHMW polyethylene remains flexible enough to smoothly conform to the foot and provide a good shoe insert. Most users wear socks, for moisture dissipation, ventilation, and sanitation reasons. The fabric of the sock comprises a weave of fibers that constitute many irregularities that readily sink into and grip a softer less dense surface. UHMW polyethylene is dense enough to resist this sinking in or deformation at the pressures typically generated by a human foot while remaining flexible enough to conform to the shape of the foot.

This material need only be utilized in thin films, preferably bonded to a substrate so as to increase flexibility even more. The substrate has a lower surface designed to prevent slipping of the insert within the shoe. For example, the lower surface may have a layer of adhesive to permanently secure the insert to the shoe. A better solution is to provide a high friction lower surface so that the insert may be removed and used in another shoe. The present invention provides an array of discrete elements releasably attached to the lower surface of the substrate. The myriad edges of the discrete elements provide increased traction to hold the insert in place. In addition, the elements may be detached and replaced with elements of different thicknesses to provide a shape modifiable orthotic device. In this way, dual benefits are synergistically derived from one design feature. The discrete elements generate friction to locate the insert and shape changeability for comfort enhancement at one and the same time.

Another advantage of the changeable thickness elements is that the user may locally reduce pressure against enlarged, sensitive or protruding portions of the foot. Heel spurs and bunions are persistent and painful conditions. Though the low friction surface of the invention reduces irritation, pressure on sensitive areas is still painful. Removing or replacing selected elements can significantly diminish the thickness overlying sensitive body parts. The enlarged or sensitive body parts have less pressure applied to them in the areas where thinner elements are used.

The discrete elements are releasably attached to the substrate by adhesive, meshing connectors such as Velcro or mechanically latching connectors such as a stud and socket arrangement. Since the elements can be of varying thicknesses, the user can custom design the insert shape depending on his foot anatomy simply by removing elements in the locations where he is experiencing discomfort. The thickness can be adjusted to correct protonation. A kit of different thickness elements can be used to create an orthotic, thus, avoiding the expensive casting-molding procedure currently in use. Elements in the kit could also be of variable Durometer.

The shoe insert may be in the form of a flat foot-shaped innersole or as a slipper containing a soft partial upper. The insert of the invention will provide significant relief from discomfort for older people and athletes. The insert is low in cost and can be used for the life of the shoe or for many shoes. The improvement in comfort and reduction of skin problems is well worth the slight increase in shoe cost. Additional advantages and features are described below with reference to the detailed description and their accompanying drawings.

DETAILED DESCRIPTION OF THE INVENTION

The shoe insert of this invention provides an innersole having an extremely low friction upper surface adjacent the foot and a high friction lower surface adjacent the shoe. The weight of the user thus frictionally anchors the insert to the shoe while allowing non-abrasive movement of the foot or stocking of the user. The low friction surface not only avoids skin irritation but also generates less heat within the confines of the shoe.

The very low friction upper surface is provided by a layer, sheet or film of a synthetic organic polymer having a coefficient of friction of no more than 0.3. Representative materials useful for this layer include fluorinated polymers like polytetrafluoroethylene, linear polyamides like nylon, and polyacetal copolymers. Especially ideal for the preferred embodiment of the invention is the UHMW-PE or ultrahigh molecular weight polyethylene described above with a weight-average molecular weight over 3 million, usually 3.5 to 4 million. These plastics are inert and safe in contact with skin, often approved for use in implantable prostheses. They are self-lubricating and have the following coefficients of friction as determined by the ASTM D 1894 test standard.

| MATERIAL | STATIC | KINETIC |
| --- | --- | --- |
| Mild Steel on Mild Steel | .30–.40 | .25–.35 |
| UHMW-PE on Mild Steel | .15–.20 | .12–.20 |
| UHMW-PE on UHMW-PE | .20–.20 | .20–.30 |

The dynamic or kinetic coefficient of friction on polished steel for dry materials for various of these plastics is compared below, again based on the ASTM D 1894 standard.

| | |
| --- | --- |
| UHMW-PE | .10–.22 |
| NYLON 6 | .15–.40 |
| NYLON 6/6 | .15–.40 |
| NYLON/MoS2 | .12–.20 |
| PTFE | .04–.25 |
| ACETAL COPOLYMER | .15–.35 |

The high friction bottom surface of the insert is provided by scoring or roughening the bottom surface or by adhering a higher friction substance thereto. For example, a thin layer of UHMW-PE could be attached to a nylon substrate by gluing, thermal bonding or laser welding. For the high friction lower surface, roughening may be achieved by adhesively fastening a fabric like cotton, porous foam material such as latex, or sprayed on flocking fibers. Alternatively, the insert may be glued into the shoe.

The top low friction layer may be very thin. A thickness as little as 0.1 mil (millimeter) is sufficient to give a long wearing low friction surface. The overall thickness of the insert need only be enough to prevent wrinkling, usually 2–10 mils, typically 3–5 mils. This insert can be folded and carried in a pocket or purse. Embodiments of the invention which incorporate thickness adjusting removable pad elements reach about 20 mils or so. For high heel shoes, a higher friction area rearward of the ball of the foot may be used to prevent the tendency of the foot to slide forward.

Figure 1:
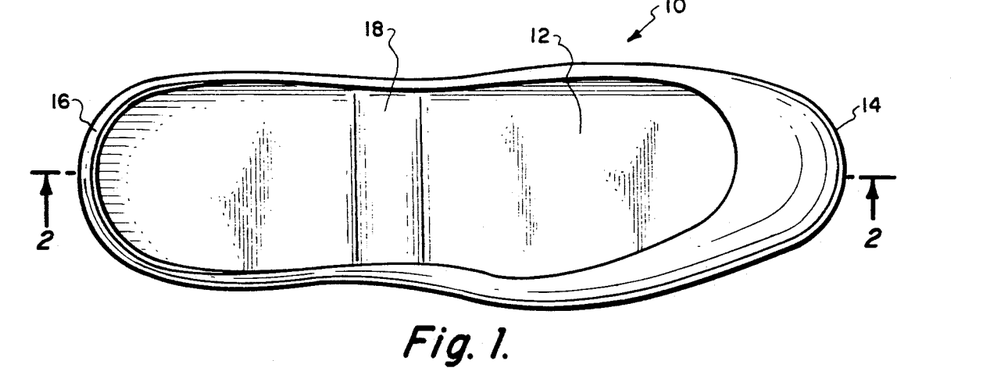
FIG. 1 is a top view in elevation of a first embodiment of a low friction shoe insert according to the invention.
Figure 2:
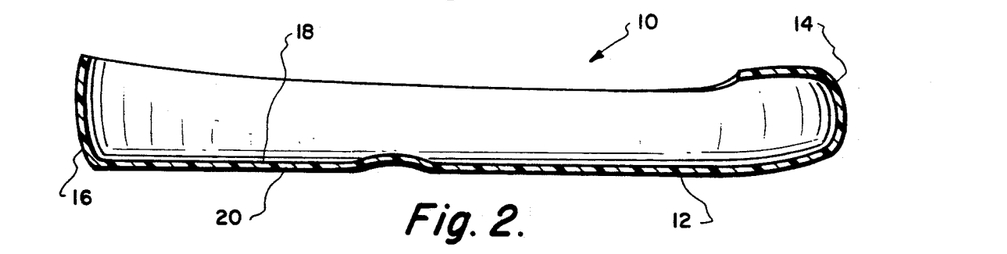
FIG. 2 is a view in section taken along line 2—2 of FIG. 1.

In FIGS. 1 and 2 a first embodiment of the invention is shown in the form of a slipper 10. The slipper has a sole 12, a toe gripping front panel 14, and a heel gripping rear panel 16. The slipper can be suitably formed from one piece of an elastomer like latex rubber. The inner surface contains a very thin layer 18 of very low friction UHMW-PE.

Figure 3:
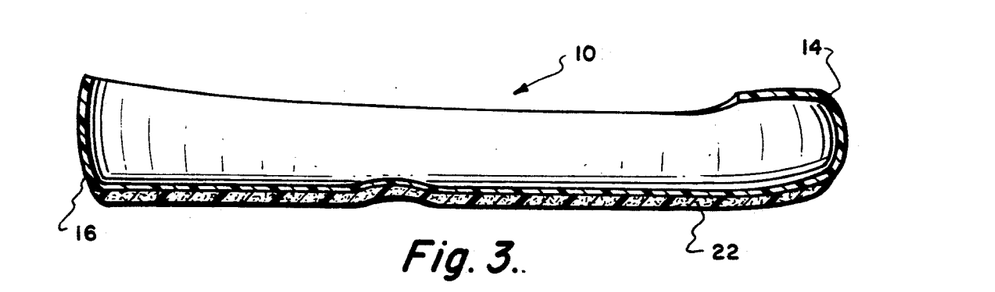
FIG. 3 is a view in section of a second embodiment of the low friction shoe insert of FIG. 1 modified to include a layer of padding on the sole.
Figure 4:
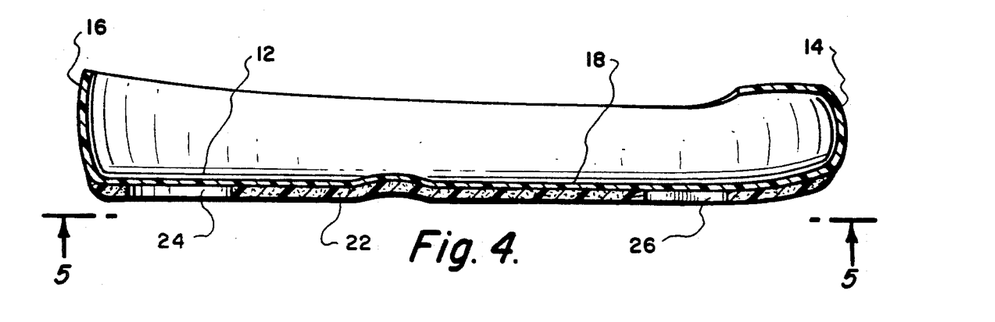
FIG. 4 is a view in section of the shoe insert of FIG. 3 modified to include cut outs or windows in the layer of padding under the heel and ball of the arch sections of the foot of the user.
Figure 5:
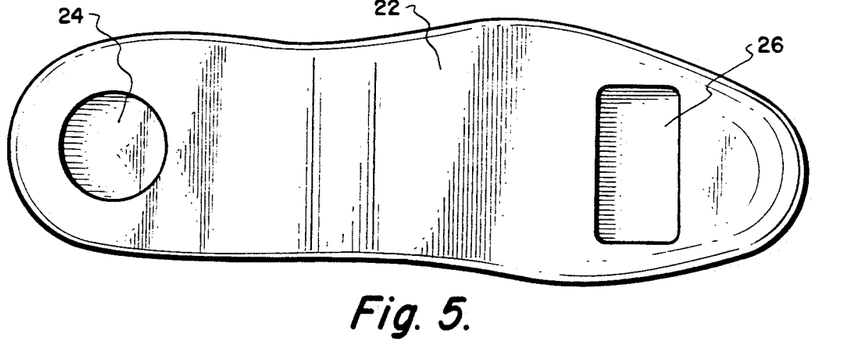
FIG. 5 is a bottom view in elevation shown in the direction of line 5—5 of FIG. 4.

If the outer surface of slipper 10 does not provide adequate anchoring to the shoe, a layer 22 of high friction cushioning material such as felt or latex foam can be applied to the bottom surface of sole 12 as shown in FIG. 3. As shown in FIGS. 4 and 5, portions of cushion layer 22 may be removed at locations 24 and 26 to relieve pressure on sensitive areas of the foot. The thin insert can expand into relieved areas 24 and 26 due to the flexible nature of the UHMW-PE.

Figure 6:
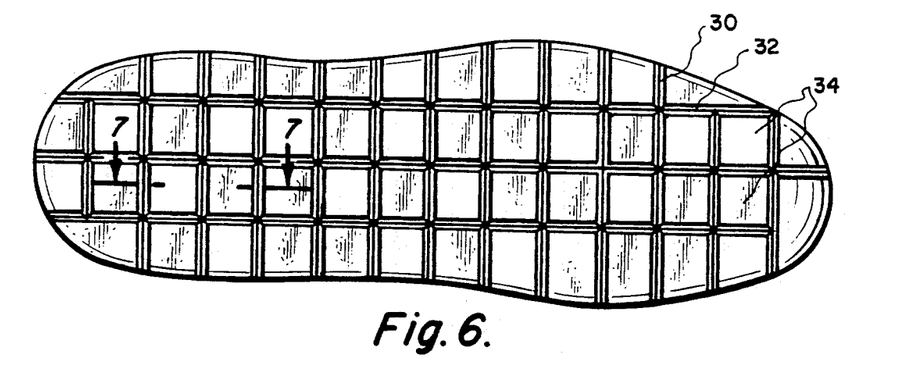
FIG. 6 is a bottom view of another embodiment of the insert of the invention in which a plurality of discrete pad elements are releasably arrayed on the bottom surface.
Figures 7, 8, 9:
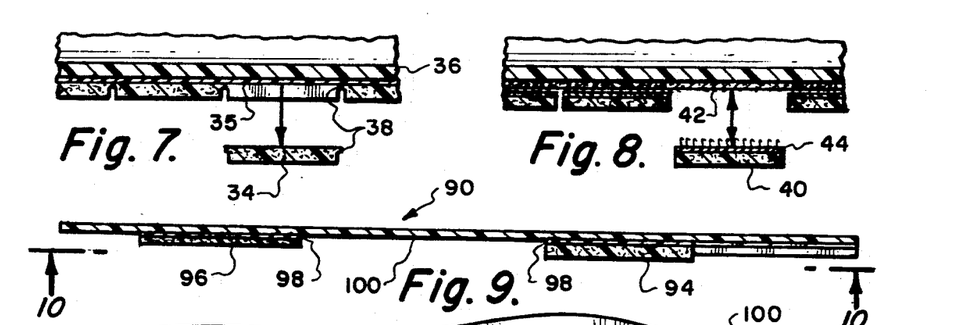
FIG. 7 is a view in section taken along line 7—7 of FIG. 6 showing how the individual pads or elements may be adhesively attached to the sole.
FIG. 8 is another view in section showing the use of Velcro to attach individual pads to the sole.
FIG. 9 is a view in section of yet another shoe insert according to the invention having adhesively adhered elements with different thicknesses.

FIGS. 6 and 7 illustrate an alternative system for providing a high friction bottom surface that can be readily modified to provide windows in the cushioning in regions of swelling, pain, or inflammation. The bottom surface of the insert has a sheet 35 of material with intersecting indentations or score lines 30 and 32 forming an array of discrete square elements 34. Sheet 35 is adhered to sole 12 by means of a pressure sensitive adhesive layer 36 which allows the elements 34 to be removed from sheet 35. As shown in FIG. 7, any element 34 can be removed by breaking the thin perimeter bridge 38 under the score lines and pulling the element 34 away from the adhesive layer 36.

The exposed adhesive layer 36 in FIG. 7 can collect dirt from inside the shoe. This is avoided in the device of FIG. 8, where discrete cushioning elements 40 are secured to the sole 12 with Velcro type fasteners. A sheet 42 of loop material can be adhered to the sole while sheets 44 of hook material are adhered to the upper surface of each element 40.

Figure 15:
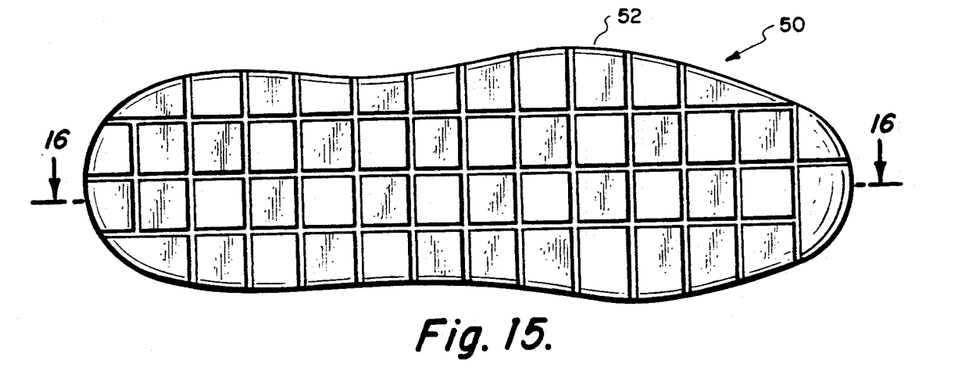
FIG. 15 is a bottom view of a further embodiment of the invention.
Figure 16:
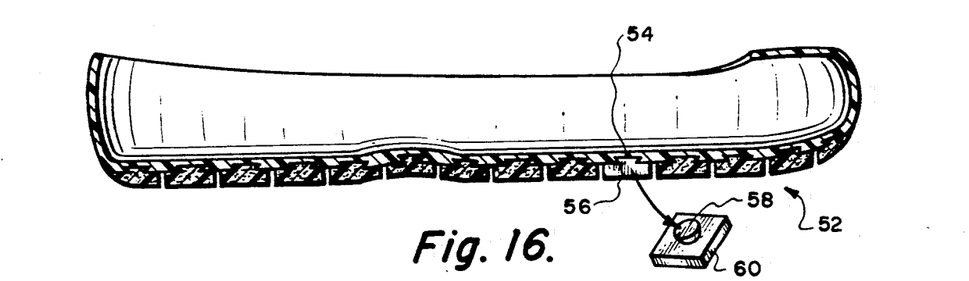
FIG. 16 is a view in section taken on line 16—16 of FIG. 15.

FIGS. 15–18 show other mechanisms for providing removable cushioning pads. In FIGS. 15 and 16, a slipper 50 has a sole 52 with a plurality of cylindrical pockets 54 that have tapered inner walls 56 adapted to engage and retain posts 58 on discrete cushion pads 60. This type of discrete pad can be removed and reattached numerous times.

Figure 17:
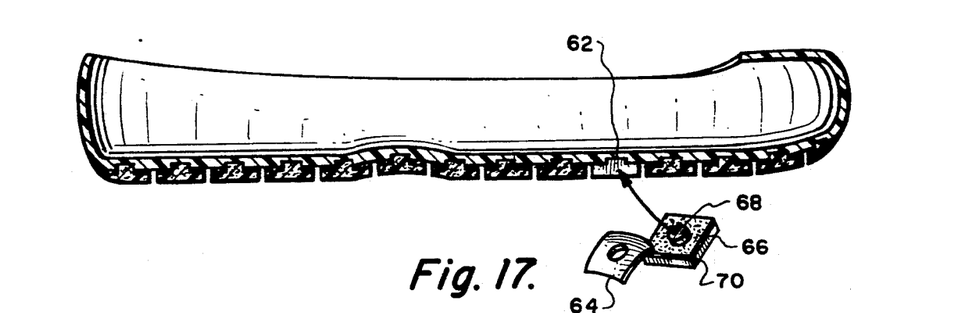
FIG. 17 is a further sectional view of the insert of FIG. 16 shown with the adhesive layer exposed.

In FIG. 17, a cylindrical socket 62 engages and centers a post 68 on a pad 70. Locking is provided by peeling off a protective sheet 64 from the upper surface of pad 70 to expose an adhesive layer 66.

Figure 10:
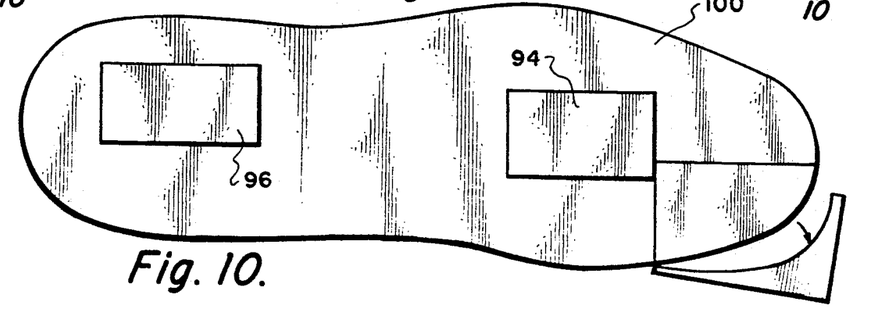
FIG. 10 is a bottom view in elevation of the shoe insert of FIG. 9 shown in the direction of line 10—10.
Figure 11:
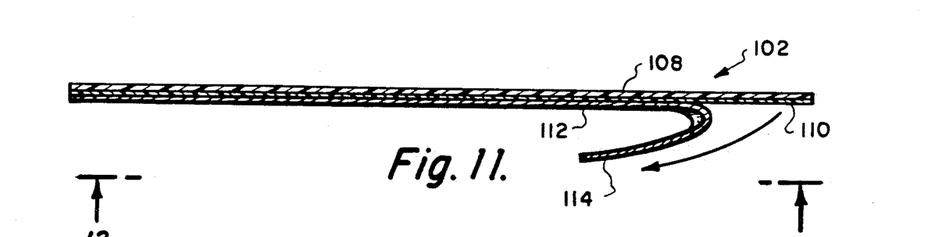
FIG. 11 is a further embodiment of the shoe insert of the invention shown in section.
Figure 12:
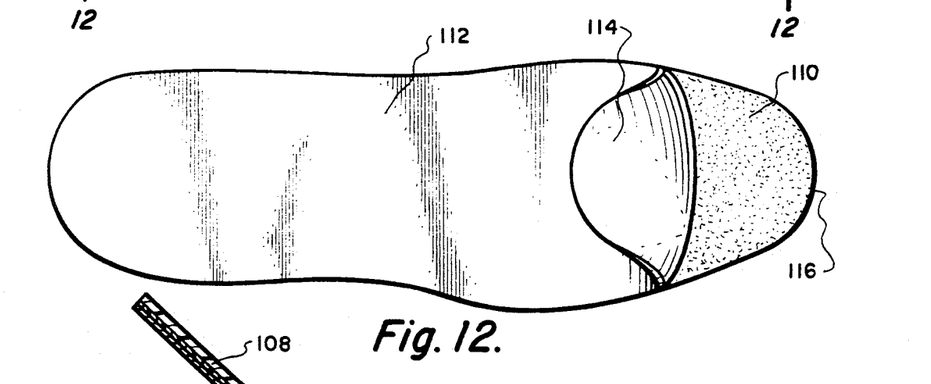
FIG. 12 is a view in elevation of the shoe insert of FIG. 9 shown from the direction of line 12—12 in FIG. 11.
Figure 18:
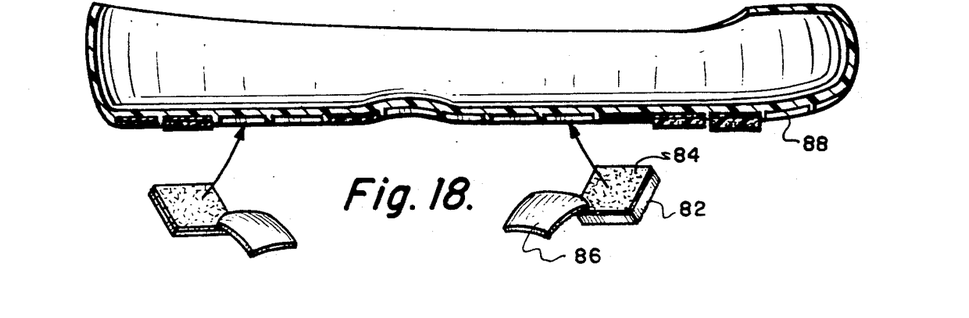
FIG. 18 is a sectional view of yet another embodiment of the invention utilizing adhesively secured pads of varying thickness.
Figure 19:
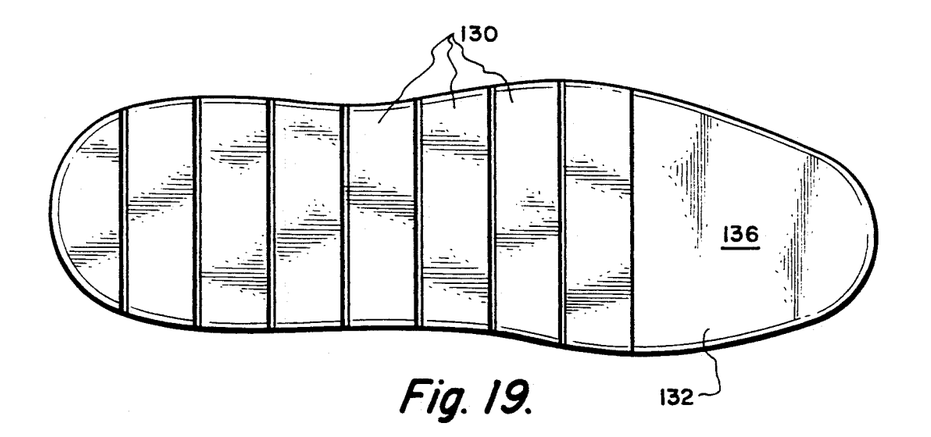
FIG. 19 is a bottom view of an insert in which the discrete detachable elements extend across the width of the insert.
Figure 20:
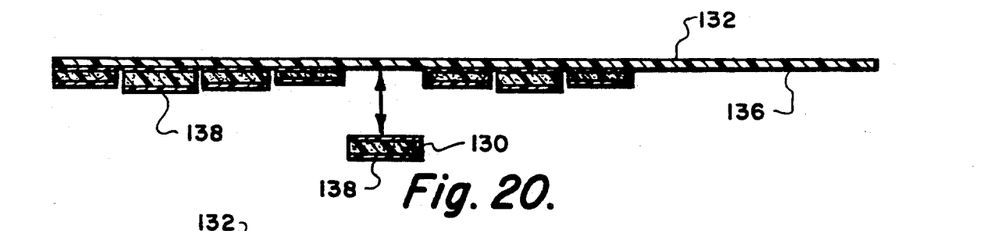
FIGS. 20 and 21 are sections of the insert of FIG. 19 showing how the different thickness elements may be adhesively or mechanically held in place.
Figure 21:
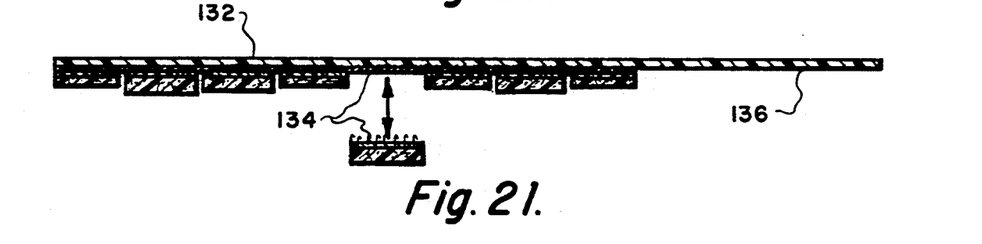

In FIG. 18, a slipper 80 has detachable pads 82 which may be of differing thicknesses. Using different selected thickness pads allows the user to correct anatomical errors in the orientation of the foot. Variable thickness pads can be attached with posts, adhesive, or Velcro but are shown in FIG. 18 connected by a layer of adhesive 84 protected by a peelable protective sheet 86. Variable thickness elements can also be fastened to a flat shoe insert 90 as shown in FIGS. 9 and 10. Insert 90 is cut from a low friction material in the shape of a shoe sole. Varying thickness pads 94 and 96 are mounted by the user in any desired location on the bottom surface 100 by a layer 98 of adhesive. Variable thickness discrete elements may also extend across the width of the insert as shown in FIGS. 19–21. Discrete detachable cushion elements 130 of varying thickness can be user positioned on the bottom surface of a low friction UHMW-PE insert 132 to custom shape the insert as desired by the user. In FIG. 20, the elements 130 are adhesively attached while in FIG. 21, Velcro materials 134 are illustrated. It has been found that cushioning is usually not needed in the toe area 136 forward of the ball of the foot. Hence, in FIGS. 19–21, the toe area cushion elements are omitted to leave more space available inside the shoe in the toe area.

Since the multiple elements have numerous edges in all of the embodiments, high friction is generated against the interior surfaces of the shoes which serves to keep the insert in the correct position. But in some situations, with many elements of several thicknesses, the friction can be so large that it is hard to move the insert in and out of the shoe. If desired, elements may be made with a smooth plastic layer like layers 138 in FIG.

20 to permit the elements to more easily slide in the shoe.

Figure 22:
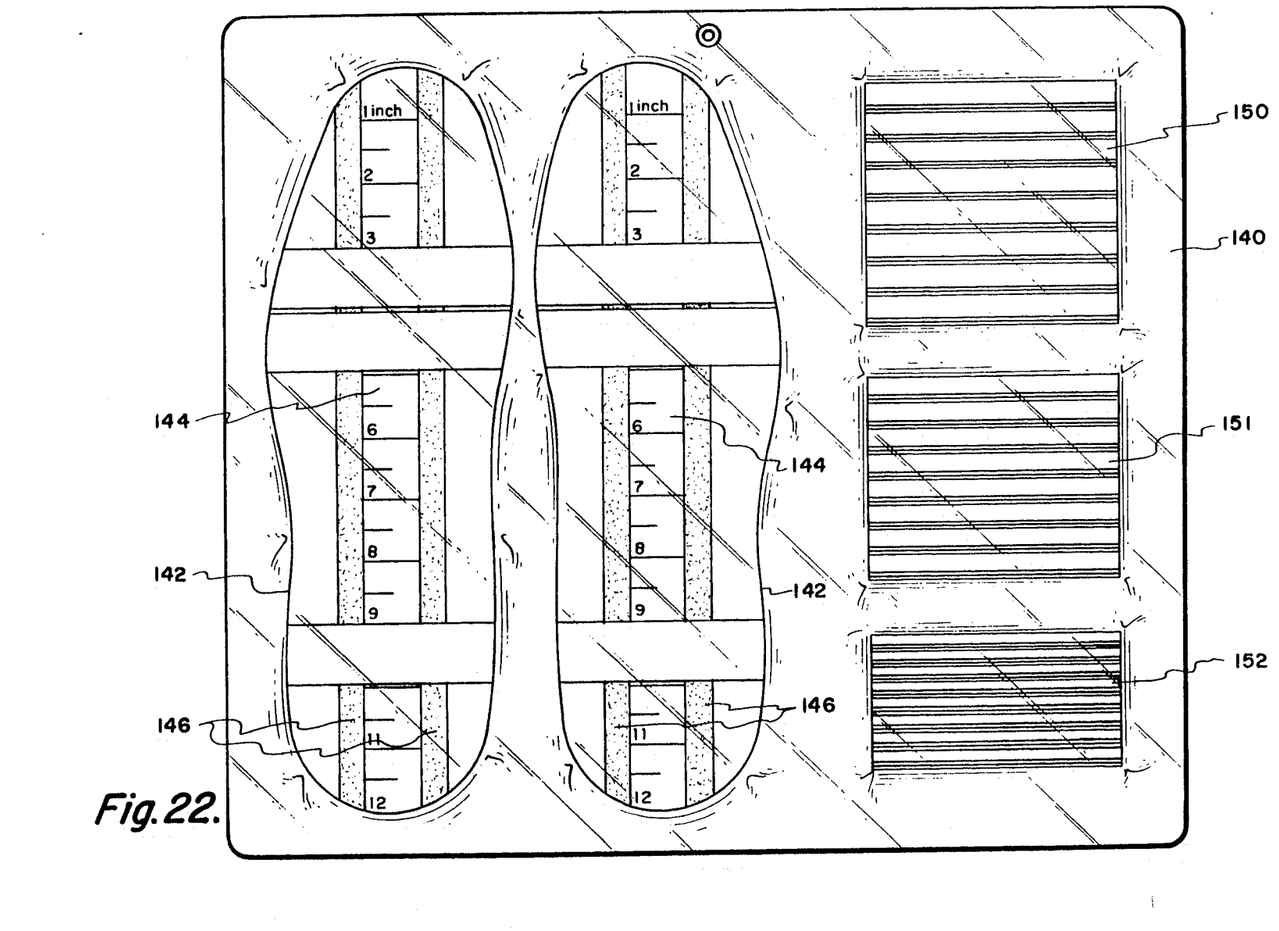
FIG. 22 shows how the insert may be provided as a kit with different thickness elements and a scale on the inserts to assist the user in correctly locating the elements.

A good way to deliver the insert to the user is shown in FIG. 22. A blister package 140 includes a pair of low friction inserts 142, each having an index scale 144 thereon, with flanking strips 146 of adhesive or Velcro type fastening material. The user may use the scale to establish and maintain the discrete and movable cushion elements at the best locations that he discovers with use. Normally the inserts would be supplied fully covered with elements, but only three per insert are shown in FIG. 22 to help make the scale visible. Three groups of replacement cushion elements 150, 151, and 152 are also included that have a variety of thicknesses to help custom shape the insert. Even if the users foot shape requirements change with time, the kit of FIG. 22 allows continuing modification of the inserts to an optimal configuration.

Figure 13:
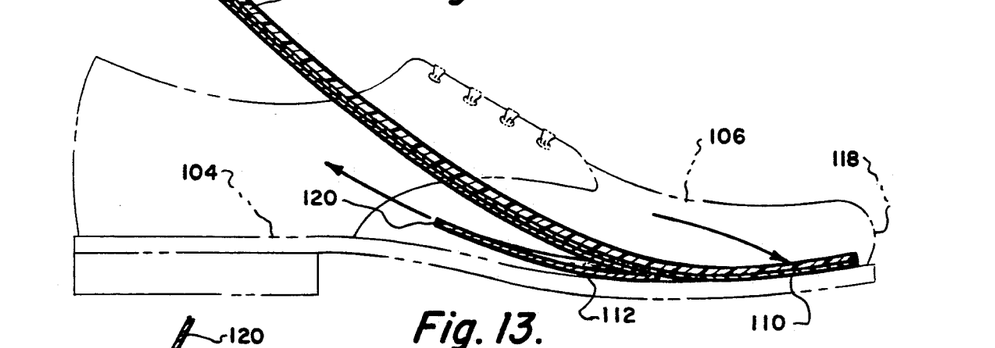
FIG. 13 is a view in section of the shoe insert of FIG. 12 shown partially inserted into a shoe.
Figure 14:
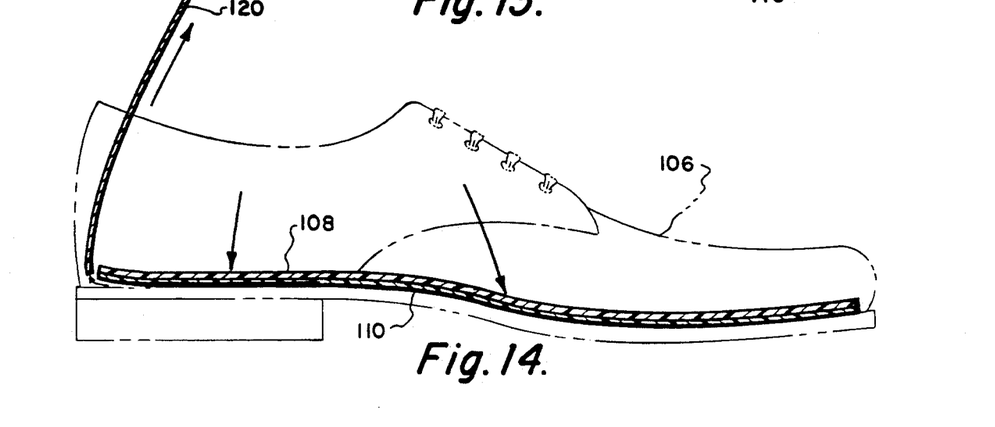
FIG. 14 is a further view in section of the shoe insert of FIG. 11 shown fully inserted into a shoe.

FIGS. 11–14 illustrate a more permanent insert 102 formed from a first layer 108 of low friction material, an adhesive layer 110, and a peelable protective sheet 112 such as paper. To install insert 102, the leading edge 114 of sheet 112 is peeled back (FIGS. 11 and 12) and the insert positioned in the shoe with the toe end 116 near front wall 118 of shoe 106 (FIG. 13). The exposed adhesive is pressed into contact with surface 104 and edge 120 of the sheet 112 extracted rearward so that the remainder of the insert can be pressed down as shown in FIG. 14.

Clearly, features described herein with respect to slipper inserts may be interchanged with those of the flat inserts as well. Because many permutations are possible, the invention should only be limited to the spirit and scope defined by the appended claims.

I claim:

1. A shoe insert comprising in combination:
   a thin sheet of low friction plastic shaped to fit over the bottom inside surface of a shoe, so as to be positioned between the shoe bottom and a foot in the shoe, said thin sheet having a top, foot contacting, low friction surface and a bottom, shoe facing, surface;
   a measurement scale on said bottom surface extending generally from the toe end of the insert to the heel end of the insert;
   strips of loop and hook fabric type fastening material, also extending generally from the toe end of the insert to the heel end of the insert, said strips positioned adjacent the sides of said scale;
   a plurality of generally rectangular detachable and replaceable cushion pad elements having hook and loop fabric type fastening material thereon, said pads being of varying thickness so that they can be mounted across said strips, in locations determined by said scale, so as to permit the thickness and shape of the insert to be adapted to the users foot.

* * * * *